(12) United States Patent
Kinsinger

(10) Patent No.: US 6,185,271 B1
(45) Date of Patent: Feb. 6, 2001

(54) HELICAL COMPUTED TOMOGRAPHY WITH FEEDBACK SCAN CONTROL

(76) Inventor: Richard Estyn Kinsinger, W349 S4698 Kingdom Dr., Dousman, WI (US) 53118

( * ) Notice: Under 35 U.S.C. 154(b), the term of this patent shall be extended for 0 days.

(21) Appl. No.: 09/249,876

(22) Filed: Feb. 16, 1999

(51) Int. Cl.$^7$ ....................................................... A61B 6/03
(52) U.S. Cl. ................................................ 378/19; 378/8
(58) Field of Search ............................. 378/4, 8, 15, 16, 378/19, 20, 207

(56) References Cited

U.S. PATENT DOCUMENTS

| | | |
|---|---|---|
| 4,965,726 | 10/1990 | Heuscher . |
| 5,164,971 * | 11/1992 | Peyret et al. ............................. 378/4 |
| 5,228,069 | 7/1993 | Arenson . |
| 5,291,402 | 3/1994 | Pfoh . |
| 5,373,543 * | 12/1994 | Ackermann et al. ................... 378/20 |
| 5,377,250 | 12/1994 | Hu . |
| 5,379,333 | 1/1995 | Toth . |
| 5,383,231 | 1/1995 | Yamagishi . |
| 5,386,446 | 1/1995 | Fujimoto . |
| 5,390,112 | 2/1995 | Tam . |
| 5,400,255 | 3/1995 | Hu . |
| 5,430,783 | 7/1995 | Hu . |
| 5,450,462 * | 9/1995 | Toth et al. ............................. 378/16 |
| 5,459,769 | 10/1995 | Brown . |
| 5,504,792 | 4/1996 | Tam . |
| 5,513,236 | 4/1996 | Hu . |
| 5,541,970 | 7/1996 | Hu . |
| 5,541,971 | 7/1996 | Saito . |
| 5,612,985 | 3/1997 | Toki . |
| 5,687,208 | 11/1997 | Bae . |
| 5,796,802 | 8/1998 | Gordon . |
| 5,818,897 | 10/1998 | Gordon . |
| 5,832,051 | 11/1998 | Lutz . |
| 5,867,555 * | 2/1999 | Popescu et al. ....................... 378/16 |
| 5,970,112 * | 10/1999 | Hsieh ..................................... 378/8 |

* cited by examiner

*Primary Examiner*—David P. Porta (57) ABSTRACT

A computer tomography apparatus for imaging an object includes a computer coupled to a data acquisition system, a carrier that traverses the object through an imaging volume, and a radiation source. In one embodiment, the computer is configured to update scan parameters based upon data received from a first subset of a detector surface. In a second embodiment, the computer is configured to reverse carrier direction and repeat the traversing of the object through the imaging volume with updated scan parameters based upon data received from the first traversing of the object through the imaging volume.

37 Claims, 9 Drawing Sheets

FIG. 1

PRIOR ART

HELICAL COMPUTED TOMOGRAPHY WITH FEEDBACK SCAN CONTROL

CROSS-REFERENCE TO RELATED APPLICATIONS

Not Applicable

BACKGROUND OF THE INVENTION

The present invention relates to a computed tomographic imaging device and a method for operating such a device in a continuous or helical mode with automatic adjustment of the device based on analysis of the data being gathered to later construct images. Computed Tomography (also called Computed Axial Tomography, CAT, or CT scanning) has evolved through several major changes, or generations, in its roughly 25 year history. The earliest scanners collimated the x-rays from a tube source into a "pencil beam" and scanned that beam linearly across the object or patient to be imaged and onto a single, synchronously moving detector, or later onto a linear array of detectors. These measurements comprised one view of the object. The tube and detector assembly (usually mounted on a rotating gantry) were then rotated a small angle around the object and another view was acquired. The steps of linear motion and rotation in a plane were repeated many times over at least 180 degrees, usually over a full circle or 360 degrees. Given enough view data in a single plane, any of several known algorithms can be used to reconstruct the planar representation of local x-ray attenuation, that is, a CT image.

A major improvement in CT occurred with adoption of so-called fan beam technology. In this advance, the x-ray beam is collimated into a nearly planar beam, tightly collimated in the axial or z-direction defining the thickness of a slice to be imaged, but spread out over an angle, called the fan angle, to cover the complete width of the object and a generally curved array of detectors on the opposite side of the object. In so-called third-generation CT designs, the detector array is usually curved, is roughly matched in azimuthal extent to the fan of x-rays, and rotates on the gantry to remain opposite the imaged object. In fourth-generation designs, the detector array covers the full arc of view data, generally a full circle, and is fixed so only a varying portion is irradiated by the x-ray fan beam as it rotates. As initially introduced, these devices acquired the full set of azimuthal views for one slice before moving the object (generally on an axially movable table) to a new slice location and acquiring data for a new planar image. For this step-and-shoot operation planar reconstruction methods are substantially correct.

The next major geometry change in CT was development of methods for helical scanning. In this advance, the scanner hardware geometry is largely unchanged—the x-ray tube and the curvilinear detector array rotate in a plane around the imaged object which is substantially perpendicular to its axis. However, now during the rotation the object is moved along the axis (usually on a moving table), so the net path of both tube and detector around the object is a helix. The axial distance covered during one gantry rotation divided by the slice thickness is called the helical pitch. Because the inter-scan delay for advancing the object is eliminated, helical scanning can cover more axial distance in a given time than the earlier step-and-shoot methods. However, because the view data for an image are no longer coplanar, image reconstruction methods must be modified to reduce the potential for artifacts. Helical scanning was introduced to commercial medical CT in the late 1980s and dominated clinical scanning protocols by the mid-1990s.

The latest major change in CT is introduction of two-dimensional or multi-row detector arrays. In this advance, the single arced row of detector cells is replaced by an array which is segmented in both the usual azimuthal direction and the axial direction. A fourth-generation scanner operating with a three-row detector is described by Heuscher et. al. in U.S. Pat. No. 4,965,726. A third-generation scanner with a two-row detector is described by Arenson et. al. in U.S. Pat. No. 5,228,069. In U.S. Pat. No. 5,291,402, Pfoh describes a general approach to multi-slice scanning in which the detector can be arranged to have any number of rows. Since these detectors can cover several slices in the axial dimension, collimation of the x-rays at the tube is opened up to cover substantially the full array; the beam has an axial (or cone) angle in addition to its azimuthal (or fan) angle. Except for the simplest case of a butted two-row detector, that of Arenson et. al. and essentially that of Heuscher et. al., the slice thickness or axial resolution then becomes determined at the detector rather than at the x-ray tube collimator. Reconstruction algorithms now must deal with data gathered from more than one row of detectors, and, of course, they are designed to produce more than one image of the object per system rotation. In addition, since the planes defined by the separate detector rows are not coplanar, further changes must be made to combat artifacts from non-coplanar data. Many special reconstruction algorithms have been developed for such helical, non-coplanar scanning, for example those described by Hu in U.S. Pat. Nos. 5,377,250, 5,400,255, 5,430,783, 5,513,236, and 5,541,970, by Tam in U.S. Pat. Nos. 5,390,112 and 5,504,792, and by Saito in U.S. Pat. No. 5,541,971.

The combination of multi-slice detectors with helical scanning compounds the challenge to dealing with non-coplanarity or incompleteness in the view data, but for small enough cone angles and small enough scan pitches these problems have been solved and this combination appears to be the technology of choice for high-end CT systems.

CT scanners today generally operate with preselected scan protocols. That is, before the start of the scan, the operator selects the volume to be covered (e.g. diameter of field of view and axial coverage) and several machine parameters (e.g. rotation speed, x-ray tube voltage, x-ray tube current, slice thickness, helical pitch, and mathematical parameters of the reconstruction algorithm, such as those which determine view filtering prior to backprojection). When these choices are made, the scan is started and proceeds to completion without change of protocol.

In some cases, large temporal changes occur in the object during the course of the scan. For example, in scans of patient cardiovascular anatomy the motion of the heart and blood or the bolus action of contrast agents injected in the vascular system produce such changes. Because standard CT reconstructions presume consistency of all views used, changes in the object during acquisition of view data will produce blurring and other significant artifacts. Several methods have been developed to deal with such temporal changes, among them those by Yamagishi in U.S. Pat. No. 5,383,231, Brown in U.S. Pat. No. 5,459,769, Toki et. al. in U.S. Pat. No. 5,612,985, Bae et. al. in U.S. Pat. No. 5,687,208, and Lutz in U.S. Pat. No. 5,832,051.

An object which is to be imaged is also typically not cylindrically uniform in space. Methods have been developed to determine spatial variations of the object in advance of a CT scan—for example, from a planar projection image called variously a scoutview or a scanogram—then predetermine and preprogram scan parameter changes which optimally account for this spatial structure. For example, Toth in U.S. Pat. No. 5,379,333 teaches a method for adjusting x-ray flux during gantry rotation around objects with high aspect ratio, such as human shoulders. Fujimoto et. al. in U.S. Pat. No. 5,386,446 teaches a method for predetermining axial regions of the object which would be best scanned with higher or lower image resolution, then preprogramming and controlling the scanner to do so in one scan operation.

In addition, during the course of a continuous or helical scan new regions of the scanned object continually enter, then progressively pass through, an imaging volume—the volume which at all times during the scan is being traversed with x-rays from the source to the detector. The imaging volume is generally a cylinder with center line on the bore of the scanner, with diameter which shadows the useful azimuthal extent of the detector, and with axial length equal to the axial x-ray beam width or that which shadows the useful axial extent of the detector, whichever is smaller. The passage of a given slice region of the scanned object across the imaging volume (i.e., the time when it is affecting the view data being gathered by the detector) may be anywhere from about half the revolution time of the gantry to several revolutions of the gantry. The view data to produce images of this new slice region is gathered over substantially all of this traverse. All of this view data is gathered using scan parameters determined before the slice region enters the imaging volume, in most cases scan parameters chosen before the start of the helical scan. If the slice region contains structures previously unknown, for example, an unlocated lesion in a human patient or a hidden flaw in a manufactured object, the predetermined scan parameters may be adequate to detect the presence of the structure, but sub-optimal for giving detailed information on it. In some cases, the user of the CT scanner may decide to do a re-scan of the object using more optimal scan parameters after images from the first scan have been produced and viewed and the location and general nature of a particular region of the object is appreciated for the first time.

In U.S. Pat. No. 5,796,802, Gordon discloses systems and methods for using a pre-specified subset of CT imaging views, generally widely spaced in projection angle, to test for the presence of target structures in the imaging volume. Only if the test indicates sufficient probability of a target structure are CT images reconstructed, or is a complete scan made if one had not been theretofore. In U.S. Pat. No. 5,818,897 the same inventor discloses a two-dimensional CT detector system with one class of detector cells for imaging and a different class of detector cells for collecting view data to be separately tested to find predetermined target structures, in one embodiment by examination of sinogram data. While Gordon's patents contain methods which test view data to find target structures, in neither invention does he address the challenge of the preceding paragraph, namely determining the presence of target structures as soon as possible after their entry into the imaging volume of a helical scan so the imaging process can continue from that point with changed and optimized scan parameters.

BRIEF SUMMARY OF THE INVENTION

In accordance with the present invention, a first embodiment is a computed tomography apparatus which includes a radiation detector, a radiation source, a carrier, a data acquisition system, and a computer. The radiation detector has opposing first and second edges, and a first surface region which forms a first subset of the radiation detector and a second surface region which forms a second subset of the radiation detector. The first surface region is located more proximate to the first edge and the second surface region is located more proximate to the second edge.

The radiation source, typically, an x-ray tube, is in spaced-apart and opposed relationship to the radiation detector. The radiation source emits x-rays upon the radiation detector such that an imaging volume is defined therebetween. A carrier which is capable of supporting an object to be imaged is translatable relative to the imaging volume such that the object traverses the imaging volume in the direction from the first edge of the radiation detector to the second edge of the radiation detector.

A data acquisition system is coupled to the radiation detector to acquire projection data from the first and second surface regions of the radiation detector relative to the object traversing the imaging volume. A computer is coupled to the data acquisition system, the carrier, and the radiation source, and the computer receives projection data from the data acquisition system and is configured to update scan parameters based upon the data received from the first surface region.

In a second embodiment of the present invention, a computed tomography apparatus includes an arrangement as generally described in the first embodiment except that the radiation detector does not necessarily include a discrete first surface region and second surface region. In this embodiment, the computer receives projection data from the data acquisition system and is configured to reverse carrier direction and repeat the traversing of the object through the imaging volume with updated scan parameters based upon the data received from the first traversing of the object through the imaging volume.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

BRIEF DESCRIPTION OF THE DRAWINGS

The invention, both as to organization and method of practice, together with further objects and advantages thereof, may best be understood by reference to the following description taken in connection with the accompanying drawings in which:

FIG. 1(*a*) is an enlarged view of a multi-row detector as contained in FIG. 1.

FIG. 1(*b*) is an enlarged view of a single-row detector as could be alternately contained in a scanner such as that of FIG. 1.

FIG. 1(*c*) is a pictorial representation of the gantry of a fourth-generation scanner in which the fixed detector array substantially surrounds the imaging volume and the x-ray source rotates relative to the detector array. This gantry arrangement is an alternative to the third-generation gantry of FIG. 1.

FIG. 2(*a*) is a pictorial representation of a multi-slice CT gantry, table and imaged object with the motion of the table in one direction, scanning head to feet on a human patient, and indicating the appropriate first or leading row of the detector.

DETAILED DESCRIPTION OF THE INVENTION

Figure 1:
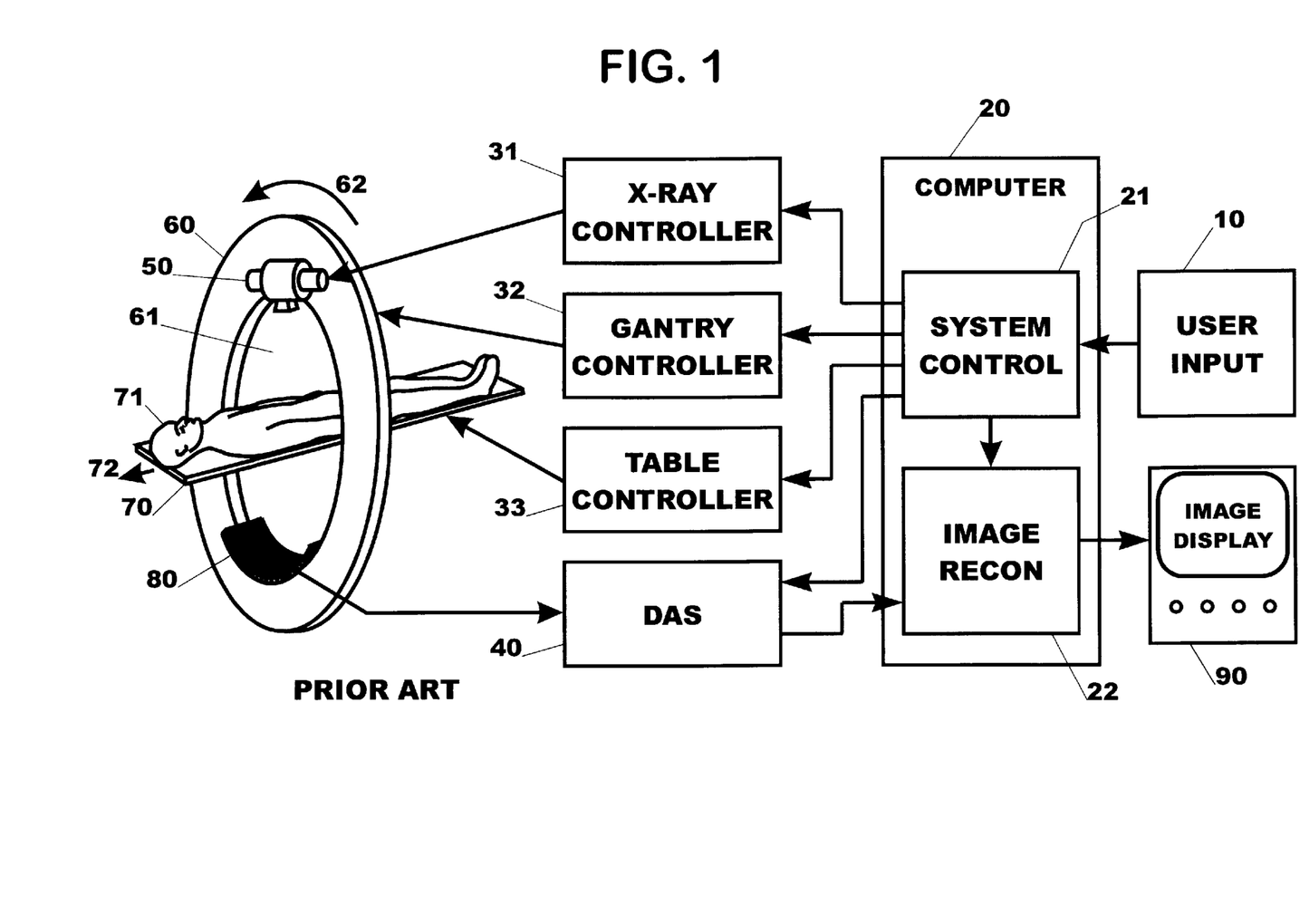
FIG. 1 is a pictorial representation of a multi-slice CT gantry, table, and imaged object and a block diagram of a control system which would be used to operate the scanner and produce images according to prior art as discussed in the Background of the Invention above.

As noted in the section BACKGROUND OF THE INVENTION, present processes for CT scanning and image reconstruction proceed from predetermined instructions and use the detector and DAS in a unified data gathering sub-process. Referring first to FIG. 1, a CT system operating using methods in the current art receives information about an object to be imaged and an instrument protocol for the scan from the operator through an operator console 10 and sends this input to a system control process 21 on a main computer 20. Hereafter an "object" or "object to be imaged" can be either a medical or veterinary patient, or an inanimate object for industrial or security inspection. The system control process 21 converts the protocol information to specific operational instructions for an x-ray subsystem, a gantry subsystem, a table subsystem and an x-ray detection subsystem and sends these instructions to the x-ray controller 31, gantry controller 32, table controller 33, and data acquisition subsystem (or DAS) 40. Collectively these operational instructions to the sub-system controllers will be referred to as "scan parameters". The controllers, in turn, send signals which initialize and determine the operation of their sub-systems through the course of the scan. An x-ray source 50, usually a generator, tube, and collimator, can be controlled as to its voltage, current and x-ray collimation. The rotating gantry 60, on which the x-ray source 50 and x-ray detector 80 are mounted, can be controlled as to its rotation speed and its angle of tilt from the axis of the carrier of the object to be imaged 70. A table or carrier 70, on which the object 71 is supported, can be controlled as to its direction and speed of translation through the gantry opening 61. An x-ray detector 80, mounted on the gantry 60 in opposition to the x-ray source 50, can be controlled as to a configuration of its elements for sampling and a frequency with which these samples are read out.

Once the scan determined by the original input to the operator console 10 has started, it proceeds to completion barring an interrupt for safety considerations. For the most common scan method, as the gantry rotates 62 around the translating 72 carrier, the x-ray source describes a helix in the frame of the carrier 70, hence the name "helical scan". As the gantry rotation proceeds, the detector is sampled at a predetermined frequency to give multiple measures of the net x-ray flux through the imaging volume. Each of these measures is collectively called a view of the object. This data is sent to the DAS 40, which in turn sends it with possible buffering to an image reconstruction process 22 in the main computer 20. This section of the computer applies an algorithm to at least 180 degrees of view data, creating an image of the x-ray attenuation in the cross-section of the imaged object 71 approximately represented by the view data. Finally, the collection of images generated by the scan is presented for operator viewing on an image display station 90.

Figure 1A:
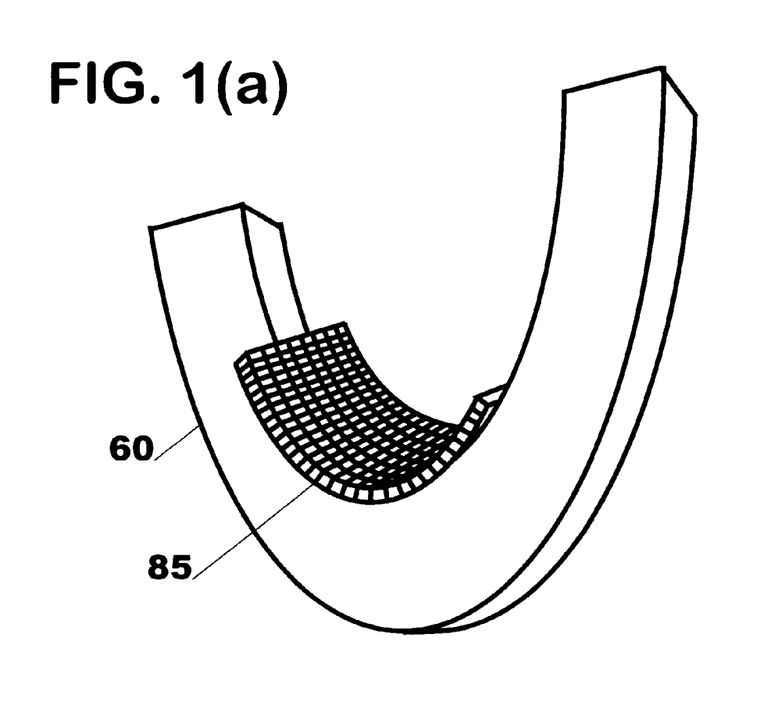

The detector represented in FIG. 1 is a segmented multi-row detector, shown in more detail in FIG. 1(a). A current system may also have a simpler single-row detector as shown for contrast in FIG. 1(b). The essentials of the system description given above would not change in this case.

Figure 1B:
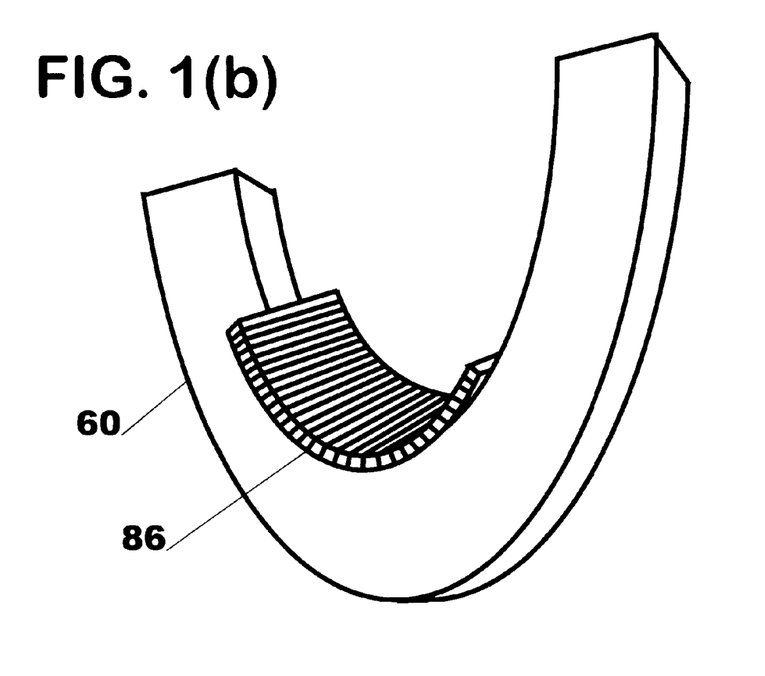
Figure 1C:
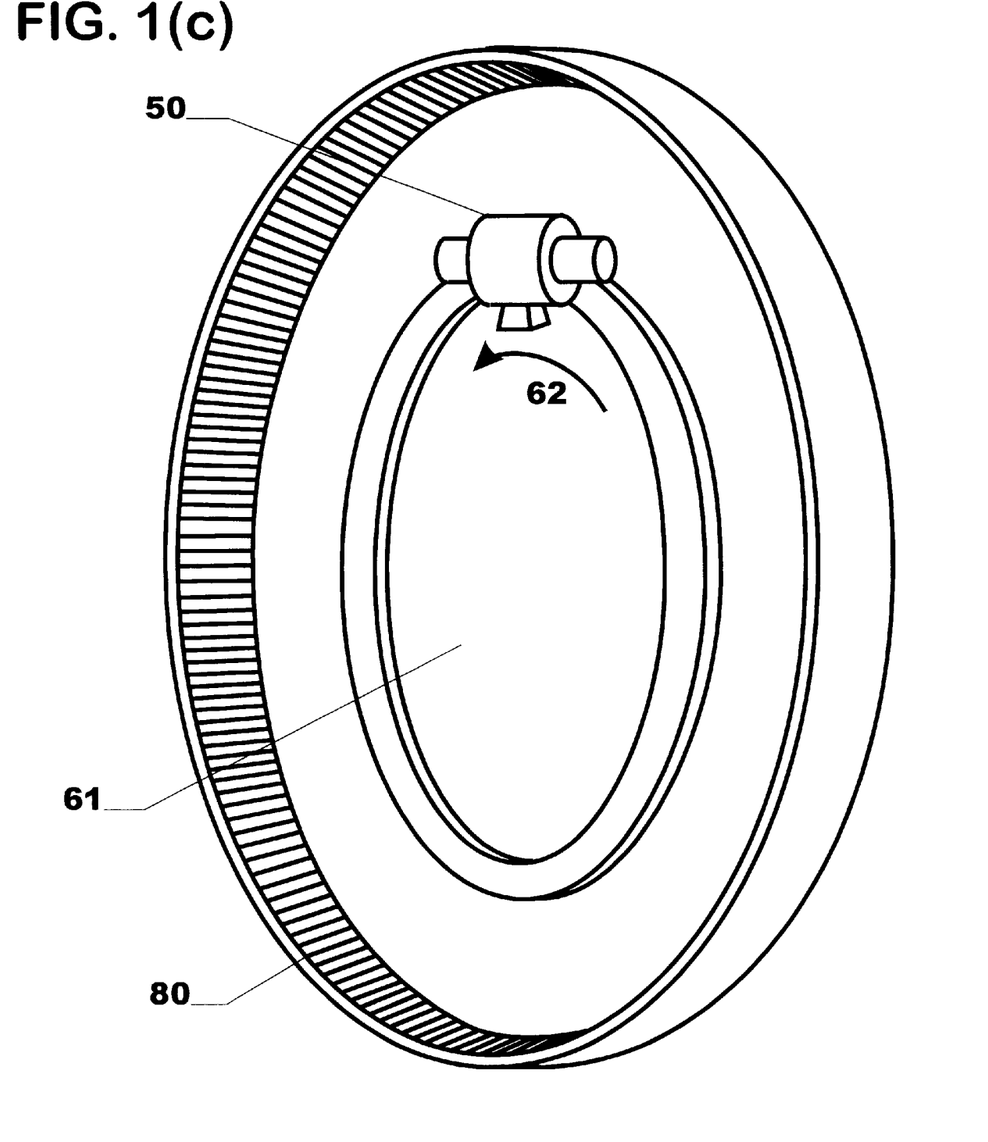

Although the prior art is described in FIG. 1 in terms of the most common third-generation or rotating gantry system, corresponding functionality will be found in fourth-generation, fixed-detector, rotating-source systems using gantry such as that shows in FIG. 1(c), and in high-speed scanners in which both x-ray source and detector hardware are fixed and the rotation of the source is caused by sweeping an electron beam on an arcuate anode in a vacuum chamber partially surrounding the gantry opening and imaged object.

An essential insight behind this invention is that in helical scanning with multi-row CT detectors there is an inherent asymmetry in the rows of the detector, an essential temporal asymmetry in the data which is gathered by these detector rows. Since the object is being advanced (by the moving carrier) through the imaging zone in one direction (for example, head-to-toe or toe-to-head), the row of detector elements on one side of the array per force receives radiation which has sampled a new region of the imaged object before the rest of the detector rows.

Figure 2A:
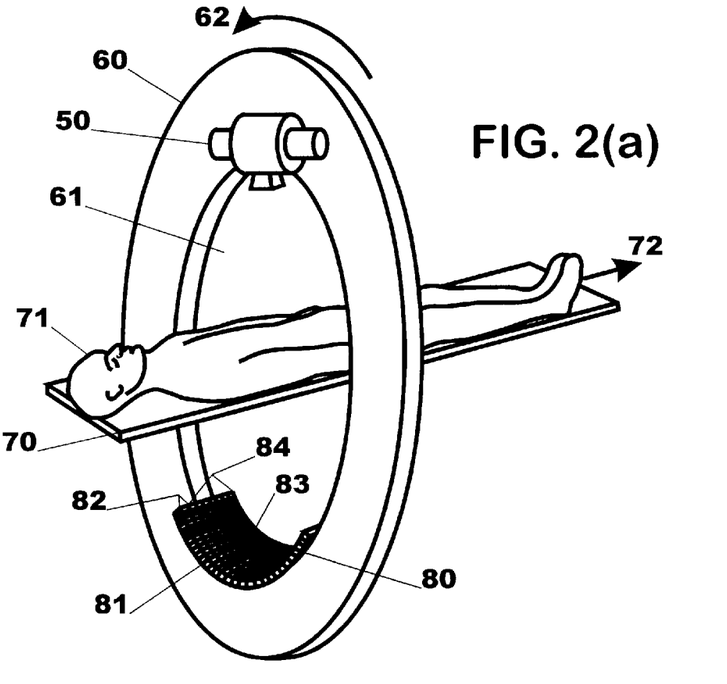
Figure 2B:
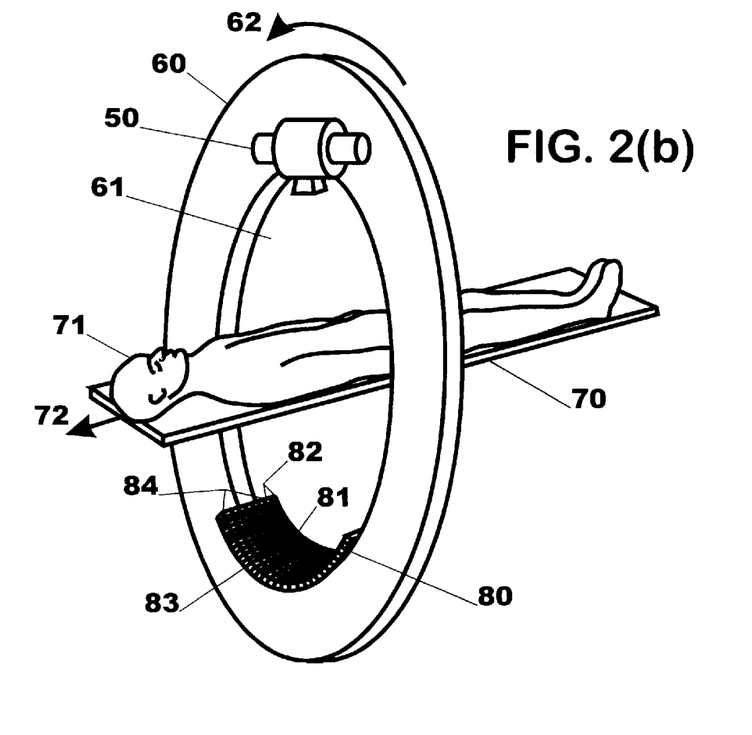
FIG. 2(b) is a pictorial representation of a multi-slice CT gantry, table and imaged object with the motion of the table in the opposite direction, scanning feet to head on a human patient, and indicating the appropriately opposite first or leading row of the detector.

This asymmetry is shown in FIG. 2(a) and FIG. 2(b). Both of these figures show a scanner with gantry 60 supporting an x-ray source 50 and x-ray detector 80. In both a carrier 70 is moving an object 71 through the gantry opening 61 while the gantry rotates in one direction 62. However, in FIG. 2(a) the carrier 70 is moving the object 71, in this example a human patient, in the foot-to-head, or inferior-superior direction, while in FIG. 2(b) the motion is reversed, head-to-toe, or superior-inferior. In both figures new material within the object is brought into the imaging volume so that a first edge of the detector 81 and a first surface region 82 of the detector next to that edge are the first to receive x-rays transmitted through that new material. However, in FIG.

2(a) that first edge 81 and first surface region 82 are on the left side of the figure, toward the patient's head, while in FIG. 2(b) the first edge and first surface region 82 are on the right side of the figure, toward the patient's feet. Correspondingly, the opposite or second edge 83 and remaining or second surface region 84 are reversed by the direction of carrier motion, as shown.

The first surface region 82 of the detector will receive an x-ray shadow from any part of the object 71 as it first enters the imaging volume. In the practice of this invention, the signals from this region are given immediate and special processing with the goal of detecting material and structures which can be imaged more optimally with scan parameters other than those currently in use. When such a detection is made rapidly and the scanner changes to new scan parameters immediately, these more optimal scan parameters will be in effect for most of the traverse of the new structure through the imaging volume. The goal is to convert to the new scan parameters before the x-ray shadow of the object passes from the first surface region 82 of the detector to the second surface region 84 of the detector, so that images of the object constructed from view data taken by this second surface region 84 will be optimized by the new scan parameters. This rapid decision process and scan parameter change is made possible by recent and continuing improvements in computer speed and affordability. As a representative calibration point, consider a scanner with 1000 views over a 0.75-second rotation using 3:1 pitch with a slice thickness equal to the width of a detector row. This scanner advances one detector row in ⅓ rotation, or 0.25 seconds, or 333 views. A leading-row view analysis and decision algorithm should operate within these constraints minus the time to implement any change in scan parameter ordered. This gives the order of a hundred views on which to base an analysis of changes in the object, and the order of a hundred milliseconds of computer time in which to do so.

Several examples can be given of structures in an object which could be detected when entering the imaging volume and which would trigger changes in scan parameters for improvement in the imaging process. For one example, if a scanner operating with scan parameters chosen for general surveying of a volume encounters a small, high-contrast structure, the scan can be altered to give detail on that object by decreasing slice thickness, decreasing scan pitch, and possibly changing x-ray energy (tube voltage) and reconstruction algorithm. For another example, if the scanner encounters an abrupt increase (or decrease) in attenuation, such as at the edge of a structure which is nearly coplanar with the scan plane, the helical pitch may be reduced and/or more weight may be given to in-plane detector rows to minimize non-coplanar artifacts. As a third example, if the scanner encounters significant increases in gross x-ray attenuation, as when the object is getting larger or denser, the x-ray flux may be increased by increasing tube current.

Figure 3:
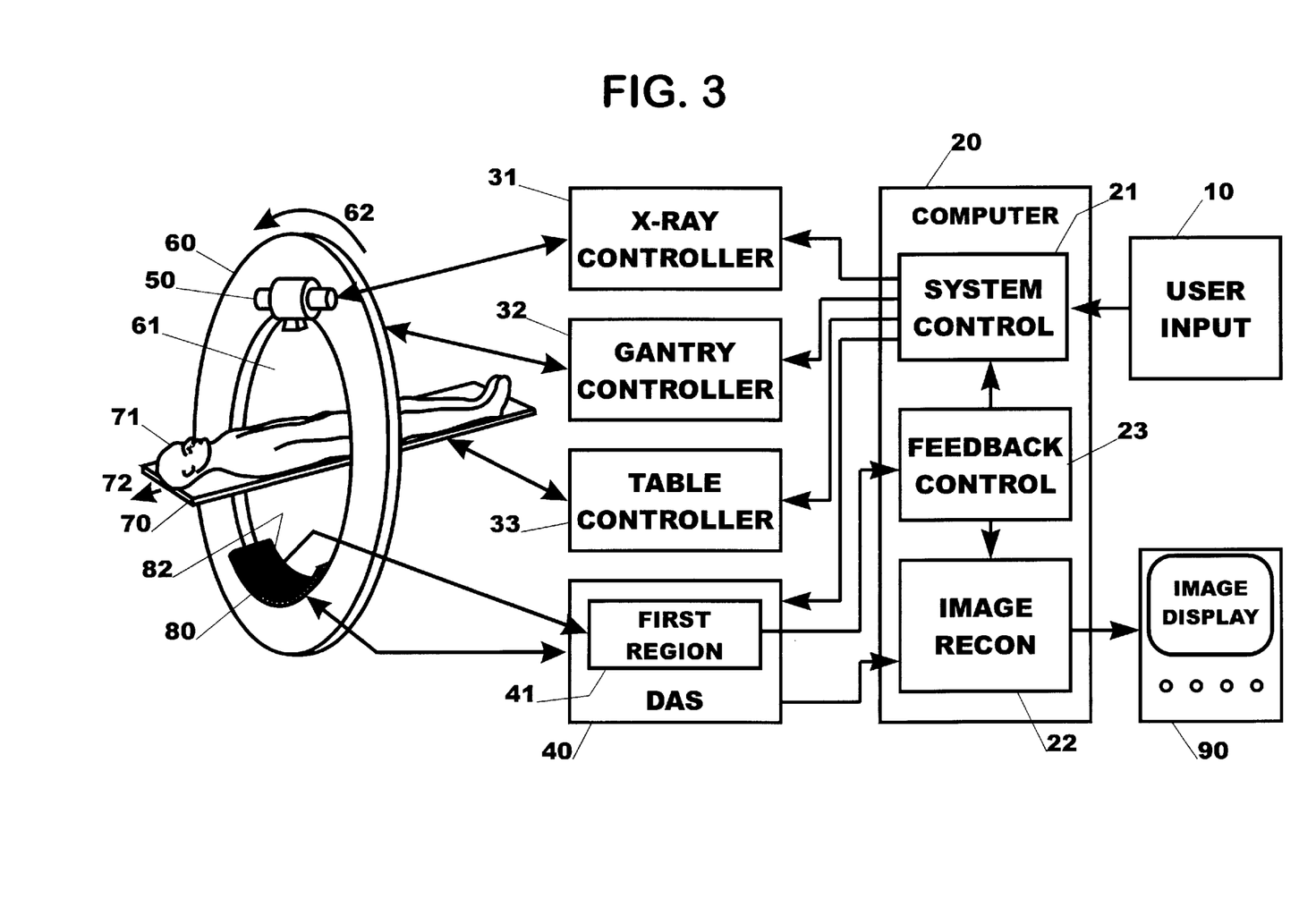
FIG. 3 is a pictorial representation of a multi-slice CT gantry, table and imaged object and a block diagram of a control system which would be used to operate the scanner and produce images according to a preferred embodiment of the present invention.

Referring now to FIG. 3, the modifications to the prior art CT system of FIG. 1 for practice of the present invention can be described as follows. Under the invention, the flow of initial input information from operator console 10, through system control section 21 of the main computer 20, through the various controllers 31, 32, 33, and 40, to the scan sub-systems 50, 60, 70, and 80 will proceed as before. A first edge 81 and associated first surface region 82 of the detector are designated based on the direction of motion of the carrier 72. When the scan starts, view data from the first surface region 82 of the detector is sent by its associated DAS processor 41 directly to a feedback control process 23, a new element in the computer 20. The full data from the detector 80 is sent through the DAS 40 to the image reconstruction process 22, as before.

The feedback control process 23 continuously tests the flow of view data from the first surface region 82 of the detector. If the test reveals a predetermined pattern in the view data that signifies entrance into the imaging volume of a predetermined structure in the object, then the feedback control process 23 selects new scan parameters and send these new instructions to the x-ray controller 31, gantry controller 32, table controller 33, DAS 40, and image reconstruction process 22. The scan proceeds using the new scan parameters until the feedback control process 23 acting on view data from the first surface region 82 detects a new condition and changes the scan parameters to new values or reverts them to the original values. Another alternative appropriate for small structures in the object is for the feedback control process to return the scan parameters to their original values after the lapse of enough time for the structure to pass through the imaging volume.

Figure 4:
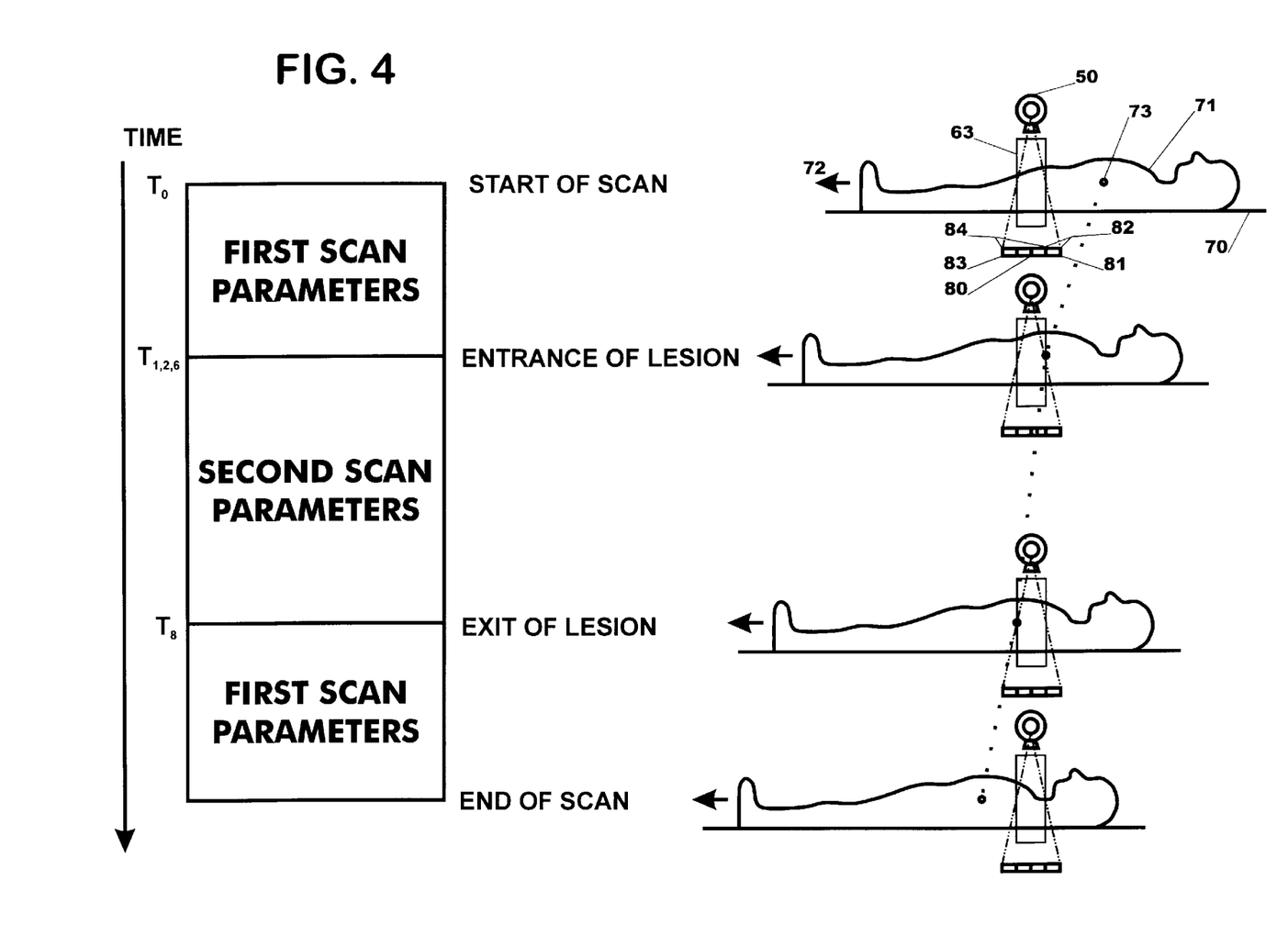
FIG. 4 is a timing diagram of significant events in the operation of a helical multi-slice CT scanner according to one preferred method of this invention, one in which the speed of transport of the imaged object is slowed on detection of a small structure in order to get higher resolution detailed images of that structure.

A representation of a simple scenario for this invention is given in FIG. 4. Here key events are shown sequentially with time flowing from top to bottom of the figure. At the start of scan, the object 71 is positioned on the carrier 70, the x-ray source 50 and opposing x-ray detector 80 defining an imaging volume 63 through which at least a segment of the object and carrier will pass. For the direction of motion 72 shown, the x-ray shadow of the object will traverse the detector from the first edge 81 to the second edge 83 as shown. The object is shown to contain a structure 73, in this example a small lesion in a patient, initially located upstream of the imaging volume 63.

The scan starts at time $T_0$. At time $T_1$, the structure 73 enters the imaging volume 63, and its presence affects the views being taken by the first surface region of the detector 82. At time $T_2$ the pattern of these views is recognized by an algorithm operating in the feedback control process 23, and at time $T_6$ the scan parameters are changed to ones more optimal for viewing the structure. Times $T_3$, $T_4$ and $T_5$ are not relevant to this scenario, but will be discussed later in this section. The total time interval for this process, $T_6-T_1$, is too small to be represented in this figure. The second scan parameters are used for the rest of the views of the structure by the first surface region, until its shadow enters the second surface region at time $T_7$, then for all imaging views taken while the structure completes its traverse of the imaging volume. In FIG. 4 the change in scan parameters is indicated by reduction in carrier speed, as would be appropriate for recording higher resolution images of a small lesion or other structure.

At time $T_8$ the structure 73 leaves the imaging volume 63 and the system may be switched back to the original scan parameters, as shown in FIG. 4, may continue with the second scan parameters, or may be switched to a predetermined third set of scan parameters. For structures which are determined to be small from the view data from the first surface region, the time $T_8-T_6$ may be approximated by dividing the detector width from first edge to second edge by the speed of carrier motion. More generally, view data from the second surface region 84, perhaps with special emphasis on detector elements closest to the second edge 83, can be examined by the feedback process of the computer in a manner fully analogous to that for entrance of new structures to detect the exit of a structure at time $T_8$.

For some CT systems with some scan parameters, a structure may pass through the first surface region of the detector and begin transit of the second surface region before it is detected and new scan parameters are set. In this case the view data from the second surface region used for imaging the structure would be recorded, at least in part, using the original sub-optimal scan parameters. Furthermore, in the case of scanners using a single-row detector, such as that shown in FIG. 1($b$), there is a single surface region; therefore, detection of a structure in the object using views must be done using the same region of the detector as is used for recording views for imaging. One option is to construct images from the view data available, perhaps giving views taken under the original scan parameters a different, lower weight in the reconstruction process.

Figure 5:
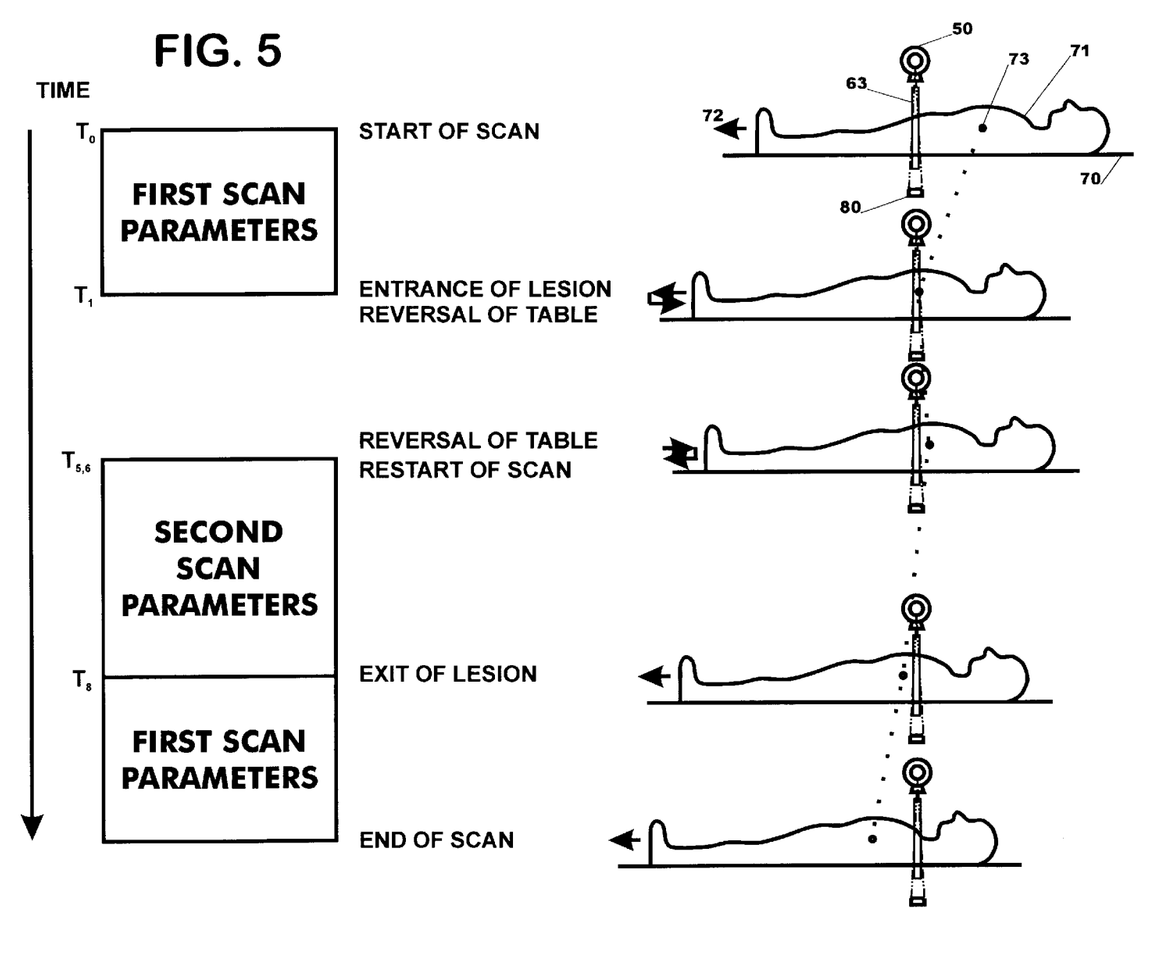
FIG. 5 is a timing diagram of significant events in the operation of a helical single-slice CT scanner according to another preferred method of this invention, one in which the table is stopped, reversed, then restored to its original direction of motion upon detection of a structure in order to obtain better images of that structure.

Another option is shown for the example of a single-row scanner in FIG. 5. As in FIG. 4, key event are shown from top to bottom of the figure. At the start of scan, the object 71 is positioned on the carrier 70, the x-ray source 50 and opposing x-ray detector 80 defining an imaging volume 63 through which at least a segment of the object and carrier will pass. The object is shown to contain a structure 73, in this example a small lesion in a patient, initially located upstream of the imaging volume 63.

Again the scan starts at time $T_0$. At time $T_1$, the structure 73 enters the imaging volume 63, and its presence affects the views being taken by the detector 80. At $T_2$ the pattern of these views is recognized by an algorithm operating in the feedback control process 23, and table motion is stopped quickly at time $T_3$. For scanning of human patients, the production of x-rays is stopped at the same time so as not to give the patient useless dose.

At time $T_4$ the table is then put in motion in the reverse direction for a time determined to remove the structure entirely from the imaging volume. At time $T_5$ the table is stopped and immediately reversed using the table speed specified under the new scan parameters. All new scan parameters, determined, as in the case of FIG. 4, to be more optimal for viewing the structure, are in effect at time $T_6$. The second scan parameters are used between time $T_6$ and time $T_8$ as views of the structure are recorded by the detector. The exit of the structure from the imaging volume, at $T_8$, may be determined in the same ways as for the case of FIG. 4, and the options for scanning beyond that time are the same as in the case of FIG. 4.

Now let us consider methods by which the feedback control process 23 of the system computer can test the view data from the first surface region 82 of the detector and detect the entry of a structure 73 into the imaging volume 63. For discussion, suppose there are M elements or cells azimuthally in the leading row of the detector, and that these elements each make one x-ray view at a rate R views per second, with V views in a complete gantry rotation taking time T=V/R. The data from the leading row of the detector may then be presented, discussed and analyzed in the plot shown in FIG. 6. The elements of the detector row (1 through M) are displayed on the abscissa or x-axis of this plot, and sequential views at R views per second are displayed in order descending on the ordinate or y-axis. The views of one gantry rotation may be labeled by view number (1 through V), time (0 through T), or view angle (0 through $2\pi$), where the x-ray source position for view angle 0 is arbitrary. In each view, each detector element yields a reading which ranges from that for full flux of x-rays to that for no x-rays. These readings, properly calibrated for gain and offset errors, are shown as gray scale values in the plot. This representation is know as a sinogram because an x-ray opaque wire orthogonal to the image plane somewhere in the scanner field of view will be represented in this plot as a sine wave centered around the middle of the x-axis range at M/2.

Figure 6:
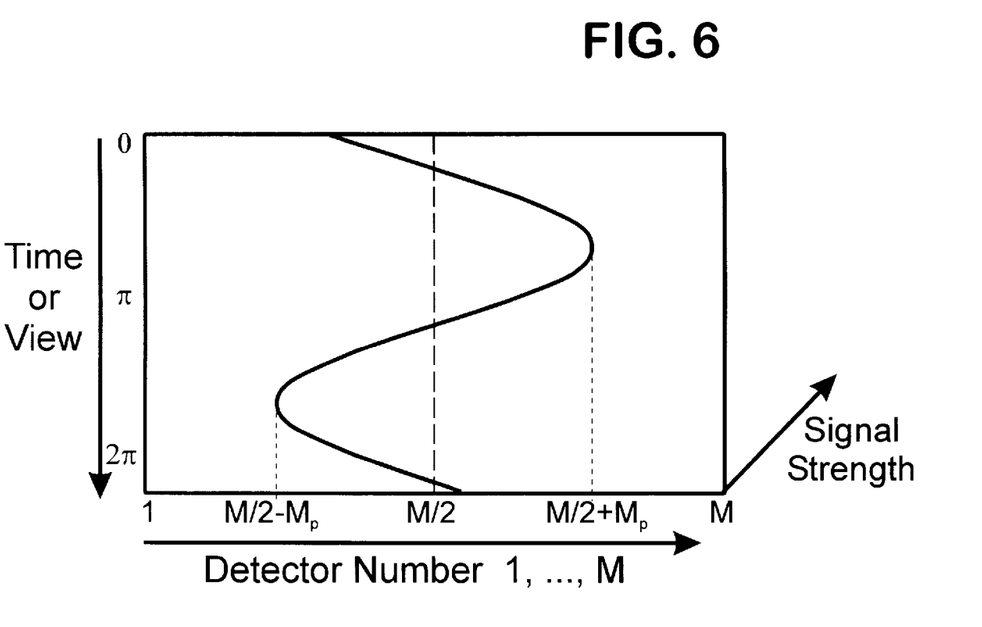
FIG. 6 illustrates a sinogram, a plot of signal across a row of detectors vs. time, in this case for a CT scan of a small wire positioned in the axial direction at a radius from the centerline of the scanner.

The x-axis amplitude, $M_P$, is proportional to the distance of the wire from the axis of scanner rotation, or isocenter. The period of all such sine waves is V in views, or T in time.

For a wire which attenuates all x-rays, the thickness of the wire in units of detector cell widths is represented by the width of the line or band in the sinogram. If the wire is less than a detector cell in thickness and/or if it is not perfectly opaque, the gray-scale value of the sine wave will be less than maximum.

For a scanner operating in helical mode, sinogram patterns will develop and fade as structures enter and pass through the detector row, or more generally the surface region of the detector, being represented. Since the sinogram evolves by adding new views in just the brief time it takes to correct new readings from each detector cell, any new structures entering the imaging volume will have their first perceptible effect in the sinogram of the leading detector row or the first surface region of the detector. In one embodiment of this invention, rapid decision algorithms may therefore be based on analysis of this sinogram.

Figure 7:
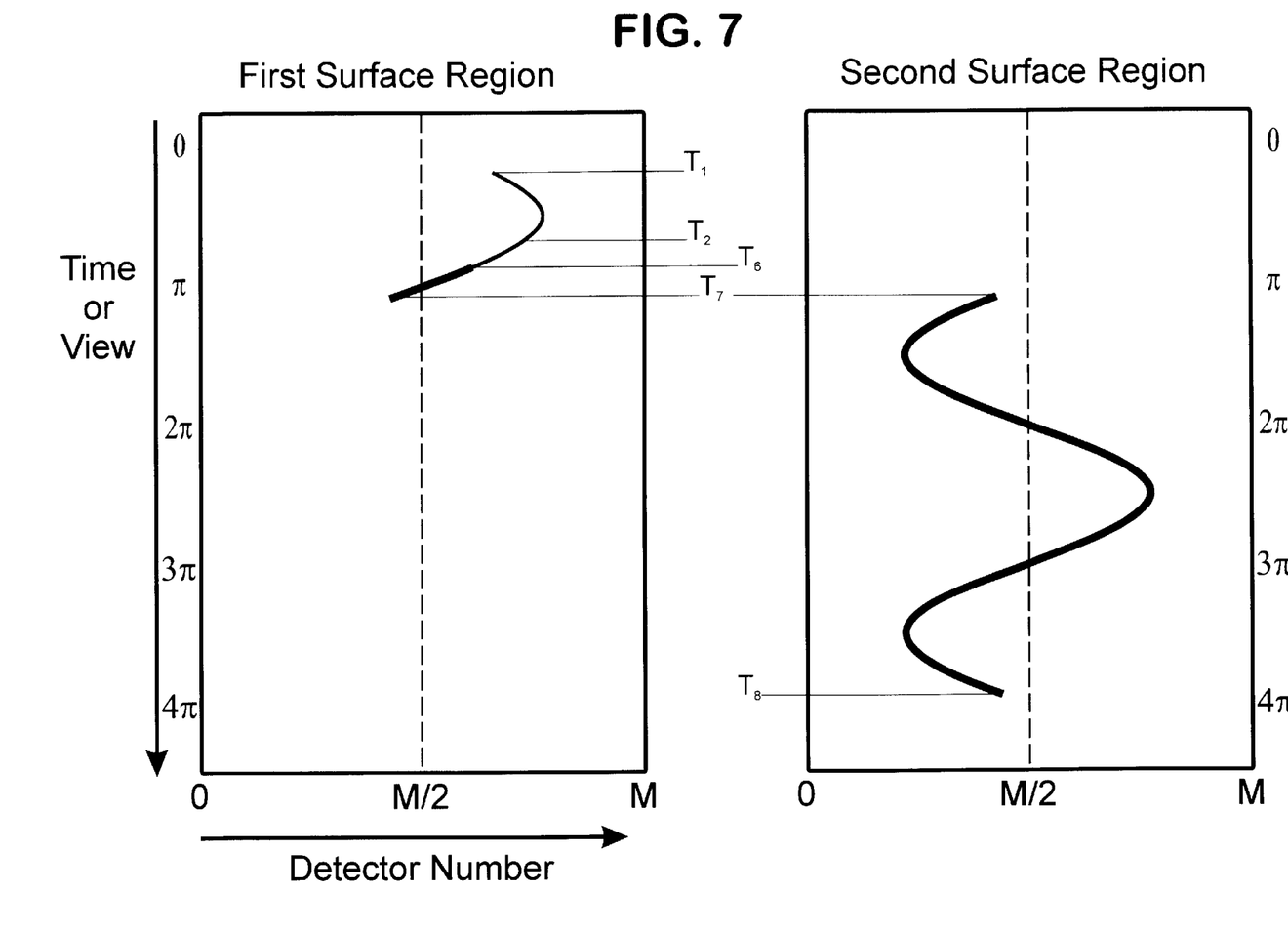
FIG. 7 shows two sinograms, one from the first surface region of a detector and one from the second surface region of the same detector, for a scan of a small opaque particle positioned at a radius from the centerline of a CT scanner as it traverses the imaging volume of the scanner. For a detector in which the second surface region comprises a plurality of contiguous and separately sampled rows of detector elements, the second sinogram of this figure is a composite of sinograms from the individual rows.

As a first example, illustrated in FIG. 7, consider a small, highly-attenuating structure in a moderately uniform and lower-attenuating region of the object. For convenience such a structure will here be called a particle. In medical imaging, a particle could be a lesion or pathological structure whose existence or location is initially being sought in a survey scan, but whose structural detail is also required for diagnosis. One example is a calcified occlusion in a coronary artery, currently believed to be a warning indicator for heart attack if the calcification is great enough. Rather than conduct a complete scan of the heart region using table speed and other scan parameters appropriate to detailed characterization of any potential calcification, using this invention a survey scan would be conducted using faster table speed and scan parameters appropriate to detection, but not detailed characterization of calcifications. If no calcification is detected through analysis of view data from the first surface region, the scan would proceed to completion in a shorter period of time than that for current CT calcification screening methods. If calcifications are detected in analysis of the view data from the first surface region, the scan parameters would be immediately changed, including slowing table motion, to those appropriate to high-resolution imaging and characterization of typical calcified lesions. In this way, the extra time required for high-resolution characterization of calcified lesions is used only for the minor fraction of screening patients in which such calcifications are actually present, resulting in a more efficient patient screening procedure.

If the x-ray shadow of a particle is one to several detector cells wide, as it crosses the first edge of the detector at time $T_1$ it will gradually begin producing a trace in the sinogram of the first surface region at an arbitrary phase of its sine wave. This situation is shown on the left portion of FIG. 7. Recall from discussion earlier in this section, in a typical situation several hundred views are recorded while the x-ray shadow of a particle traverses a detector row. Even for a particle with a shadow as small as one detector width in the azimuthal direction—perhaps $\frac{1}{10}^{th}$ of the axial length—it will take several tens of views for the particle's shadow to cross fully onto the detector. A detection algorithm has a significant volume of affected view data to use for its decision.

One effective way to process this data is to apply a time filter to highlight the temporal changes of new material entering the imaging volume and spatial filtering to extract (sinusoidal) patterns of change. The simplest and fastest time filter is a subtraction of sequential views, giving a row of data in which detector cells which are shadowed by unchanging regions of the object give null values and cells on which the x-ray shadow of the object is increasing (or decreasing) give a positive (or negative) values. For enhancement of signal-to-noise, the time filter may be extended to cover several views. In this way the systematic changes in signal from a structure moving into the imaging volume can be separated from stochastic view-to-view noise due to photon statistics, electronic noise, or small general movements of the object.

In the time-filtered data space, entry of a small highly-attenuating particle can be recognized as a signal which is narrowly spiked in the spatial direction, across detector cells. Such a spike can be found by any of several methods well known in signal analysis art, for example subjecting the result of spatial filtering to a threshold test, or finding amplitude and width of the largest time-filtered data points. Persistence of a spike over a predetermined number of views can be used as a further test for the entry of a new particle.

If persistence of a spike over a large enough number of views is used as a test, the analysis must account for shifting of the particle shadow on the detector due to gantry rotation—the sinusoidal pattern of the sinogram. Since this will be a piecewise continuous motion, the earliest views can be tested for nearly linear shifts in the spike across the detector space from view to view. If a linear shift in the shadow pattern is established, it may be used to forecast the location of the particle shadow over the next view(s). If tracking and analysis are conducted over a views representing enough angle of gantry rotation, the motion of the spike will reflect the non-linearity of the sine wave. At this point, three or more points in sinogram space may be fit to a sine wave with two undetermined parameters, amplitude (MP), and phase. As noted above, the period—V in views, or T in time—is known. Continued tracking of a spike along this sine wave can give more confidence in the presence of a shadowing particle and a fix on its location in the object (axial position, radius, and azimuthal angle).

In the example of FIG. 7, the presence of the particle is detected from the sinogram of the first surface region using view data between $T_1$ and $T_2$. At $T_2$ the particle is detected and very shortly thereafter, at $T_6$, the scan parameters are changed, represented schematically in this figure by a darkening of the sinogram trace of the particle. At $T_7$ the shadow of the particle crosses from the first surface region of the detector to the second surface region. A composite sinogram for the second surface region is shown on the right side of FIG. 7 to illustrate that the scanner gathers a full set of view data on the particle from the second surface region using the second scan parameters. In practice view data from the second surface region is used for reconstruction of optimized images and not examined as sinograms, except for the possibility of using such sinograms to determine the exit of the particle from the imaging volume at $T_8$.

As a second example of an algorithm to detect changes in the object advancing into the imaging volume, consider a frontal change of x-ray attenuation extending across substantially the entire object orthogonal to the axis of helical scanning. A structure of this sort would be found at the inferior edge of human lungs, the superior edge of the liver, or an abrupt axial change in the composition of an industrial object. If an increase in x-ray attenuation is great enough, the consequent reduction in x-ray flux at the detector will produce unacceptably low signal-to-noise in the resulting images. By detecting this situation in views from the first surface region, the image quality degradation can be avoided by adjusting scan parameters appropriately, for example by increasing x-ray tube current and thus x-ray flux. If a decrease in x-ray attenuation is great enough, the consequent increase in x-ray flux at the detector will overrange the detector yielding image artifacts. Again, by detecting this situation in views from the first surface region, the x-ray flux can be decreased or other scan parameter adjustments made.

As before, an effective analysis of the view data can start with time filtering. In this case, a useful method would be to examine a view rate of change of the detector cell values smoothed over several views to reduce stochastic noise. If this rate of signal increase (or decrease) is nearly the same across a large number of contiguous cells, if the cell-to-cell differences are less than a threshold percent, then a decision can be made that a broad frontal change in the object is entering the imaging volume. For a broad enough front, no sine wave analysis is necessary, so this case is simpler than the first example. This decision method could be slightly modified to handle changing fronts which are large but not complete across the object, or which are somewhat tilted with respect to the scan axis.

A third example is the case in which the overall lateral size of the object increases (or decreases) as it enters the imaging volume. As in the second example, this change will increase or reduce the overall attenuation of x-rays and therefore reduce or increase the flux of x-rays at the detector. When detected, image quality will be improved by scan parameter changes similar to those of the second example.

In any view, the boundary of the object is given by the outermost detectors which receive an attenuated flux of x-rays. In normal scanning the object will be laterally bounded inside the imaging volume, and the extreme detector cells, cell I and cell M in FIG. 6($a$), will receive the full, unattenuated flux of x-rays from the source. This will be true of some cells inboard from these extremes until cells which are shadowed by the outer boundary of the object are reached. The readings of these cells will be more than a threshold value different from the readings at the extremes. As the views evolve, the position of these cells can be tracked and used to detect changes in the lateral size of the object.

These three examples should be considered as illustrative of the situations which can be analyzed by proper treatment of sinogram data from a leading row or first surface region of the detector. Other analysis algorithms, some using sinogram data, some not, can be designed for these and other situations. The inventive concept of testing view data from the first surface region to detect changes in the object is not limited to any particular set of these test algorithms.

While the invention has been described in detail herein in accord with certain preferred embodiments thereof, many changes and modifications therein may be effected by those skilled in the art. Accordingly, it is intended by the appended claims to cover all such modifications and changes as fall within the true spirit and scope of the invention.

I claim:

1. A computed tomography apparatus comprising:
   a radiation detector having a first edge and a second edge in opposed relationship to the first edge, the radiation detector including a first surface region and a second surface region, each of the first and second surface regions forming a subset of the radiation detector, the first surface region being located more proximate to the first edge than the second surface region;
   a radiation source in spaced-apart and opposed relationship to the radiation detector, the radiation source emitting radiation upon the radiation detector such that an imaging volume is defined between the radiation source and the radiation detector;

a carrier which is capable of supporting an object to be imaged, the carrier and the imaging volume being translatable relative to each other such that the object traverses the imaging volume in the direction from the first edge of the radiation detector to the second edge of the radiation detector;

a data acquisition system coupled to the radiation detector to acquire projection data from the first and the second surface regions of the radiation detector relative to the object traversing the imaging volume; and a computer coupled to the data acquisition system, the carrier, and the radiation source, the computer receiving projection data from the data acquisition system and being configured to update scan parameters based upon data received from the first surface region.

2. The computed tomography apparatus of claim 1 wherein the carrier is capable of translation in two directions and further wherein the first surface region and the second surface region are defined by the direction of translation.

3. The computed tomography apparatus of claim 1 wherein the radiation detector is an array of detector elements and the first surface region is at least one row of detector elements and the second surface region is at least one row of detector elements.

4. The computed tomography apparatus of claim 1 wherein the radiation detector is more than one row of detector elements with at least one gap separating two rows.

5. The computed tomography apparatus of claim 1 wherein the radiation source is an x-ray tube and the radiation emitted is x-rays, and the computed tomography apparatus further comprises a gantry upon which the x-ray tube is rotatably mounted, the imaging volume being defined within a circumference of a bore defined by rotation of the x-ray tube and the carrier translating axially through the bore.

6. The computed tomography apparatus of claim 5 wherein the computed tomography apparatus further comprises a collimator positioned between the x-ray tube and the object, the collimator having an opening to control the axial spread of the x-rays.

7. The computed tomography apparatus of claim 5 wherein the radiation detector is generally arcuate and rotates collectively with the x-ray tube on the diametrically opposing portion of the bore.

8. The computed tomography apparatus of claim 5 wherein the radiation detector is generally arcuate and stationary relative to the gantry and extends substantially around the circumference of the bore.

9. The computed tomography apparatus of claim 5 wherein the scan parameters are selected to include at least one from the group consisting of: rotation speed of the x-ray tube, voltage applied to the x-ray tube, current applied to the x-ray tube, angle of tilt between the gantry plane and the direction of the carrier motion, axial translation speed of the carrier, readout configuration of the radiation detector and data acquisition system, a frequency with which the data acquisition system acquires data from the radiation detector, and mathematical parameters of an image reconstruction algorithm.

10. The computed tomography apparatus of claim 6 wherein the the scan parameters are selected to include at least one from the group consisting of: rotation speed of the x-ray tube, voltage applied to the x-ray tube, current applied to the x-ray tube, angle of tilt between the gantry plane and the direction of the carrier motion, axial translation speed of the carrier, readout configuration of the radiation detector and data acquisition system, a frequency with which the data acquisition system acquires data from the radiation detector, mathematical parameters of an image reconstruction program, and the width of the collimator opening.

11. A computed tomography apparatus comprising:

a radiation detector having a first edge and a second edge in opposed relationship to the first edge, the radiation detector including a first surface region and a second surface region, each of the first and second surface regions forming a subset of the radiation detector, the first surface region being located more proximate to the first edge than the second surface region;

an x-ray tube in spaced-apart and opposed relationship to the radiation detector, the x-ray tube emitting x-rays upon the radiation detector;

a carrier which is capable of supporting an object to be imaged, the carrier and the imaging volume being translatable relative to each other such that the object traverses the imaging volume in the direction from the first edge of the radiation detector to the second edge of the radiation detector;

a gantry upon which the x-ray tube is rotatably mounted such that an imaging volume is defined within a circumference of a bore defined by rotation of the x-ray tube and the carrier translating axially through the bore;

a data acquisition system coupled to the radiation detector to acquire projection data from the first and the second surface regions of the radiation detector relative to the object traversing the imaging volume; and a computer coupled to the data acquisition system, the carrier, the gantry, and the radiation source, the computer receiving projection data from the data acquisition system and being configured to update scan parameters based upon data received from the first surface region.

12. The computed tomography apparatus of claim 11 wherein the radiation detector is an array of detector elements and the first surface region is at least one row of detector elements and the second surface region is at least one row of detector elements.

13. The computed tomography apparatus of claim 11 wherein the radiation detector is more than one row of detector elements with at least one gap separating two rows.

14. A method for scanning an object by helical scan operation of a computed tomography apparatus having a multiple-row detector array, the method comprising the steps of:

selecting scan parameters for start of a helical scan including direction of motion of the object through an imaging volume;

designating a leading row of the detector array based on which detector elements will be first exposed to radiation traversing a part of the object as it enters the imaging volume;

processing projection data from the leading row of the detector array to test for patterns of signal changes as the scan is progressing; and updating the scan parameters if the evolving patterns of signal change are found to meet a predetermined criterion.

15. The method of claim 14 wherein the step of processing projection data compromises processing data from at least one row of the detector array in addition to the leading row.

16. The method of claim 14 wherein the step of processing projection data includes testing an evolving dynamic range of detector signals from the leading row of the detector array against at least one threshold value.

17. The method of claim 14 wherein the step of processing projection data includes testing an evolving minimum of detector signals from the leading row of the detector array against at least one threshold value.

18. The method of claim 14 wherein the step of processing projection data includes applying pattern recognition algorithms to the data as evolving sinograms.

19. The method of claim 14 wherein the step of processing projection data includes comparing the pattern of signal changes from the detector to representative patterns which are generated by at least one of the following events: entry into the imaging volume of a small, highly-attenuating structure in the object, entry into the imaging volume of a large region of the object with significant change in radiation attenuation, entry into the imaging volume of a region of the object with large planar variations in radiation attenuation, change in lateral size of a region of the object with attenuation greater than a threshold value, change in lateral size of a region of the object with attenuation below a threshold value, and change in overall lateral size of the object.

20. The method of claim 14 further comprising the steps of a return to the step of processing projection data from the leading row of the detector array and at least one repetition of the last two listed steps.

21. The method of claim 14 further comprising the step of returning the scan parameters to their previous values after a time interval substantially equal to the axial width of the imaging volume divided by the speed of the imaged object through the imaging volume.

22. The method of claim 14 wherein the step of designating a leading row of the detector array also entails designating an opposed trailing row of the detector array, and the step of changing the scan parameters also entails processing the projection data from the trailing row of the detector array to test for patterns of signal changes as the scan is progressing, and these steps are followed by the step of returning the scan parameters to their previous values if the evolving patterns of signal change are found to meet predetermined criteria.

23. An image created by helical scan operation of a computed tomography apparatus having a multiple-row detector array according to the following steps:
selecting scan parameters for start of a helical scan including direction of motion of the object through an imaging volume;
designating a leading row of the detector array based on which detector elements will be first exposed to radiation traversing a part of the object as it enters the imaging volume;
processing projection data from the leading row of the detector array to test for patterns of signal changes as the scan is progressing; and
updating the scan parameters if the evolving patterns of signal change are found to meet a predetermined criterion.

24. A computed tomography apparatus comprising:
a radiation detector;
a radiation source in spaced-apart and opposed relationship to the radiation detector, the radiation source emitting radiation upon the radiation detector such that an imaging volume is defined between the radiation source and the radiation detector;
a carrier which is capable of supporting an object to be imaged, the carrier and the imaging volume being translatable relative to each other such that the object traverses the imaging volume during a tomographic imaging scan of the object;
a data acquisition system coupled to the radiation detector to acquire projection data from the radiation detector relative to the object traversing the imaging volume; and
a computer coupled to the data acquisition system, the carrier, and the radiation source, the computer receiving projection data from the data acquisition system during a tomographic imaging scan and being configured to process this data and based on the results of the processing continue the tomographic imaging scan or repeat the tomographic imaging scan of at least a portion of the object with updated scan parameters.

25. The computed tomography apparatus of claim 24 wherein the radiation detector is a row of detector elements.

26. The computed tomography apparatus of claim 24 wherein the radiation source is an x-ray tube and the radiation emitted is x-rays, and the computed tomography apparatus further comprises a gantry upon which the x-ray tube is rotatably mounted, the imaging volume being defined within a circumference of a bore defined by rotation of the x-ray tube and the carrier translating axially through the bore.

27. The computed tomography apparatus of claim 26 wherein the computed tomography apparatus further comprises a collimator positioned between the x-ray tube and the object, the collimator having an opening to control the axial spread of the x-rays.

28. The computed tomography apparatus of claim 26 wherein the radiation detector is generally arcuate and rotates collectively with the x-ray tube on the diametrically opposing portion of the bore.

29. The computed tomography apparatus of claim 26 wherein the radiation detector is generally arcuate and stationary relative to the gantry and extends substantially around the circumference of the bore.

30. The computed tomography apparatus of claim 26 wherein the scan parameters are selected to include at least one from the group consisting of: rotation speed of the x-ray tube, voltage applied to the x-ray tube, current applied to the x-ray tube, angle of tilt between the gantry plane and the direction of the carrier motion, axial translation speed of the carrier, readout configuration of the radiation detector and data acquisition system, a frequency with which the data acquisition system acquires data from the radiation detector, and mathematical parameters of an image reconstruction algorithm.

31. The computed tomography apparatus of claim 27 wherein the scan parameters are selected to include at least one from the group consisting of: rotation speed of the x-rav tube, voltage applied to the x-ray tube, current applied to the x-ray tube, angle of tilt between the gantry plane and the direction of the carrier motion, axial translation speed of the carrier, readout configuration of the radiation detector and data acquisition system, a frequency with which the data acquisition system acquires data from the radiation detector, mathematical parameters of an image reconstruction program, and the width of the collimator opening.

32. A method for scanning an object by helical scan operation of a computed tomography apparatus, the method comprising the steps of:
selecting scan parameters for start of the helical scan;
moving the object through an imaging volume;

processing projection data from a row of a detector to test for patterns of signal changes as the scan is progressing; and stopping the helical scan if the evolving patterns of signal change are found to meet a predetermined criterion.

33. The method of claim 32 further comprising the steps of:

reversing the direction of motion of the object for the time necessary to return the object a predetermined distance from where the object stopped; and restoring the object to its original direction of motion and restarting a helical scan with updated scan parameters.

34. The method of claim 33 further comprising an iterative return to the step of processing projection data from a row of a detector.

35. The method of claim 33 further comprising the step of returning the scan parameters to their previous values after a time interval substantially equal to the axial width of the imaging volume divided by the speed of the object through the imaging volume.

36. An image created by helical scan operation of a computed tomography apparatus according to the following steps:

selecting scan parameters for start of the helical scan;

moving the object through an imaging volume;

processing the projection data from a row of a detector to test for patterns of signal changes as the scan is progressing; and stopping the helical scan if the evolving patterns of signal change are found to meet a predetermined criterion.

37. The image created according to the steps of claim 36, wherein the steps further include:

reversing the direction of motion of the object for the time necessary to return the object a predetermined distance from where the object stopped; and restoring the object to its original direction of motion and restarting a helical scan with updated scan parameters.

* * * * *